United States Patent
Shannon et al.

(10) Patent No.: US 7,689,003 B2
(45) Date of Patent: Mar. 30, 2010

(54) COMBINED 2D AND 3D NONDESTRUCTIVE EXAMINATION

(75) Inventors: Robert E. Shannon, Oviedo, FL (US);
Clifford Hatcher, Orlando, FL (US);
Claudio Laloni, Taufkirchen (DE);
Frank Forster, München (DE);
Fredrick M. Davis, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 954 days.

(21) Appl. No.: 11/455,523

(22) Filed: Jun. 19, 2006

(65) Prior Publication Data

US 2007/0217672 A1    Sep. 20, 2007

Related U.S. Application Data

(60) Provisional application No. 60/784,106, filed on Mar. 20, 2006.

(51) Int. Cl.
*G06K 9/00* (2006.01)
*G01N 21/00* (2006.01)
*G01N 21/84* (2006.01)

(52) U.S. Cl. .................. 382/108; 356/73.1; 356/426

(58) Field of Classification Search ........... 382/108, 382/112, 115, 152, 154, 141, 145, 147; 356/238.1, 356/426, 601, 602, 603, 610, 73.1, 139.09, 356/237.1, 241.1, 241.2, 604; 700/118, 303
See application file for complete search history.

(56) References Cited

U.S. PATENT DOCUMENTS 6,741,734 B2 * 5/2004 Sasaki et al. ............... 382/149

6,813,035 B2 * 11/2004 Hoffmann ................... 356/603
7,315,644 B2 * 1/2008 Macy et al. ................. 382/154
7,356,449 B2 * 4/2008 Hashash ........................ 703/7
7,357,028 B2 * 4/2008 Kim ............................ 73/627

(Continued)

FOREIGN PATENT DOCUMENTS

EP    0 970 435 B1    3/1998

(Continued)

OTHER PUBLICATIONS

"Spatial Integrated Systems", "3DIS", "Revolutionary Digital 3D Image and Data Capture System", "Model 1500"; [online]; [retrieved Feb. 23, 2006]; 7 pages; Retrieved from http://www.sisinc.org/pring.asp?id=12; Spatial Integrated Systems, Inc. Rockville, MD.

*Primary Examiner*—Abolfazl Tabatabai

(57) ABSTRACT

An inspection apparatus (10) applying two dimensional nondestructive examination images onto a three dimensional solid model of a component (12) to display a virtual component (73) that may be manipulated to perform a nondestructive inspection. The two dimensional nondestructive examination images may be acquired from a plurality of views of the component in order to provide full coverage of the surface to be inspected, with appropriate stitching of images in regions of overlap between adjacent views. The two dimensional images (62) may be color or black and white photographs or ultraviolet or infrared images, for example. Multiple types of nondestructive examination images, results of inspection data evaluations, and design, operational and/or maintenance information may be displayed separately or jointly on the three dimensional solid model. Surface features of interest that are mapped as defined areas (76) on the three dimensional solid model may be displayed simultaneously in different views on 2D and 3D images of the virtual component.

16 Claims, 4 Drawing Sheets

U.S. PATENT DOCUMENTS

| | | | |
|---|---|---|---|
| 2003/0059103 A1* | 3/2003 | Shiomi et al. | 382/144 |
| 2005/0030525 A1 | 2/2005 | Forster et al. | |
| 2005/0068544 A1 | 3/2005 | Doemens et al. | |
| 2005/0238206 A1 | 10/2005 | Doemens et al. | |
| 2006/0098212 A1 | 5/2006 | Forster et al. | |
| 2006/0250503 A1* | 11/2006 | Crutchfield et al. | 348/207.99 |

FOREIGN PATENT DOCUMENTS

WO    WO 2005/080916 A1    9/2005

\* cited by examiner

COMBINED 2D AND 3D NONDESTRUCTIVE EXAMINATION

CROSS-REFERENCE TO RELATED APPLICATION

This application claims benefit of the Mar. 20, 2006, filing date of U.S. provisional application No. 60/784,106.

FIELD OF THE INVENTION

This invention relates generally to the field of nondestructive examination (NDE), also known as nondestructive evaluation, nondestructive inspection (NDI), and nondestructive testing (NDT).

BACKGROUND OF THE INVENTION

A wide variety of nondestructive techniques are used to gather data and to provide condition assessment reports for industrial components. Standards for such examinations are defined by organizations such as the American Society for Nondestructive Testing (ASNT), the American Society for Testing of Materials (ASTM), the American Society for Mechanical Engineering (ASME), the American Welding Society (AWS), the International Standards Organization (ISO) and other national and international entities. NDE techniques are available for the inspection of surface conditions (e.g. dimensional measurement and visual inspection), for the inspection of near-surface and surface-opening conditions (e.g. dye penetrant test, magnetic particle test and thermography), and depending upon the material of construction of the component, for full volumetric inspection (e.g. eddy current test, ultrasonic test, radiographic test).

Experience shows that a majority of the information and data available for diagnostics and prognostics, and the data most directly relatable to the assessment of component condition, comes from visual inspections and dimensional measurements. There may be over one hundred visual examinations and inspections required during the manufacturing and service life of a typical gas turbine component, for example.

To augment traditional manual visual inspections, it is known to utilize the capabilities of modern optical imaging devices together with computers and software in systems often referred to as aided visual inspections, and to combine such inspections with mechanical or automated control systems, known as machine vision systems. Such systems may include an electro-mechanical, hydraulic or pneumatic manipulator and they may function automatically to measure and to evaluate components. Automatic label checkers, container fill level measurement systems, and assembly or misalignment detectors are examples of such systems.

Machine vision systems have been used in the control of mechanical equipment and in facial recognition systems in security applications. There are many known systems that facilitate dimensional measurement and inspection of industrial components. Such systems are typically equipped with the capability of acquiring surface position information and the capability of converting such information into three dimensional data files. The data files, in turn, may be rendered as three dimensional wire frames, as having an artificial surface applied, or as three dimensional solid models of the component using known engineering design and three dimensional image processing software.

BRIEF DESCRIPTION OF THE DRAWINGS

The present invention is explained in the following description in view of the drawings that show.

DETAILED DESCRIPTION OF THE INVENTION

The present invention expands upon known dimensional and visual inspection techniques by integrating nondestructive inspection information with a three-dimensional model of a component to provide a novel capability for true virtual space inspection. In one embodiment, the invention combines two dimensional visual inspection data with three dimensional surface position inspection data to map acquired 2D optical images onto viewed surfaces of a 3D digital model of a component. The result is a true virtual 3D image of the real component, including optical images of degradations, defects and other conditions observable during a visual inspection of the component. Once the virtual component is created in virtual space, a human inspector can manipulate the virtual component to perform a visual inspection of the virtual component. The results of such an inspection can be recorded in the virtual space, including virtual marking directly onto the virtual part. The inspector can perform the virtual inspection to include all of the manipulations that are commonly accomplished during a manual visual inspection of the real component. In addition, embodiments of the invention also permit the inspector to enhance the inspection, such as with zoom imaging; hue, saturation and/or luminance manipulation; layering of additional forms of inspection data and/or evaluation results onto the virtual component; automatic evaluation techniques; and other data enhancement, data comparison, and statistical analysis techniques. The present invention allows the virtual component to be archived for later comparison with similar information for the same component at a point in time later in the component's life after the original component condition has been changed, or for comparison with similar information for other similar components. The present invention allows the results of the inspections (i.e. component condition assessments) that are created by the human inspector using the inspector's training and experience, combined with graphical user interface (GUI) image processing operations or automated image processing operations, to be recorded as additional surface mapping features on the virtual 3D image of the real component. The present invention also allows the results of the inspections to be created by automated image processing, expert system, and related artificial intelligence algorithms to be recorded as additional surface mapping features on the virtual 3D image of the real component. In addition, inspection results may be archived and recalled for various comparisons, to track condition assessment changes through the partial or entire lifecycle of a component or a population of components, or for the comparison of various components or groups of components with design, operational, service and/or repair history data.

Figure 1:
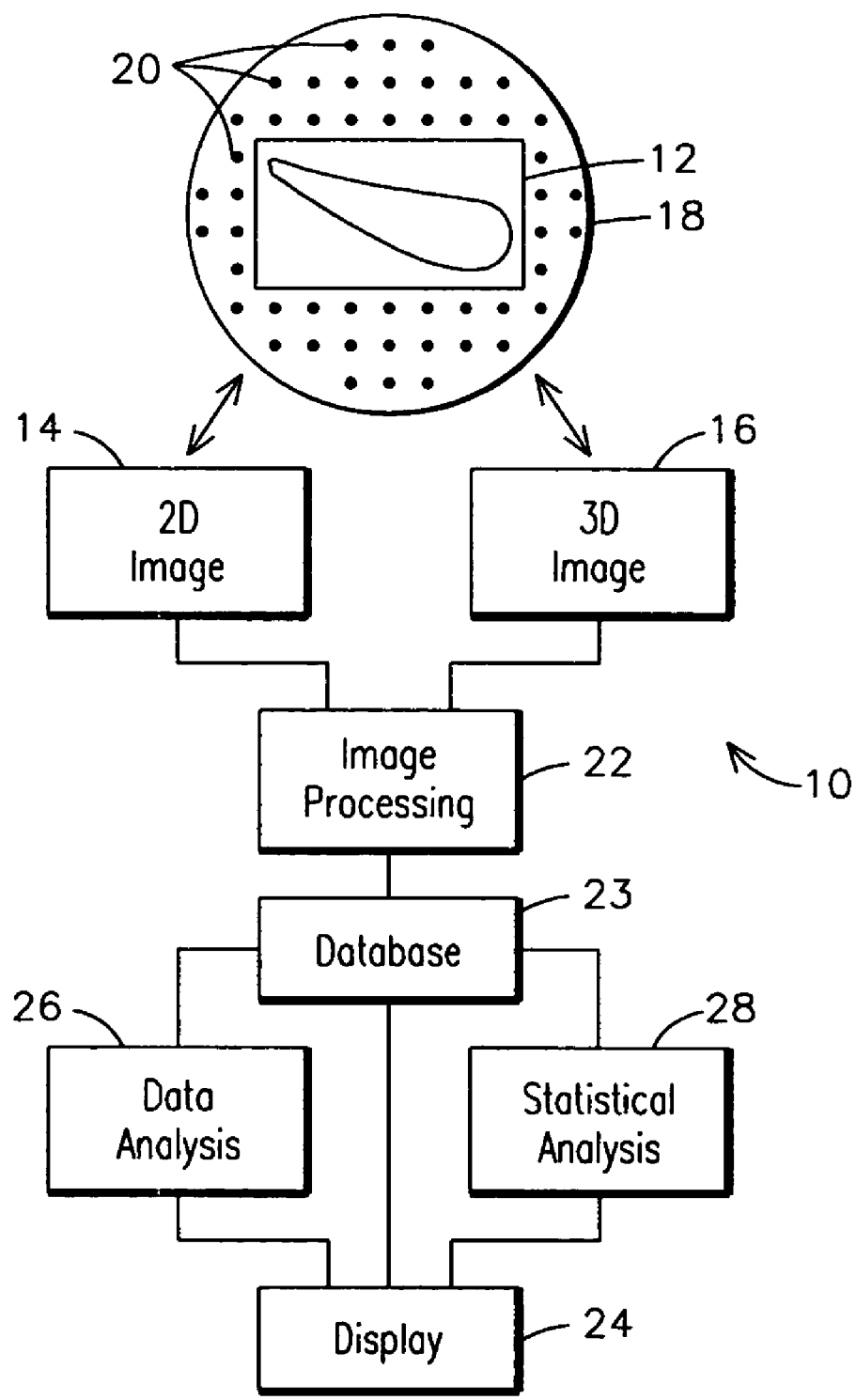
FIG. 1 is a block diagram of an inspection apparatus.

FIG. 1 is a block diagram representing one embodiment of the present invention. An inspection apparatus 10 is used to perform a virtual inspection of an industrial component 12, such as a gas turbine blade. The inspection apparatus 10 includes a 2D nondestructive inspection element 14, for example a known digital photography apparatus and a 3D dimensional measurement element 16, for example the structured light panoramic scanner described in United States Patent Application Publication US 2005/0068544 A1, which is hereby incorporated by reference herein. Both the 2D and 3D data collection may be accomplished with the same hardware in some embodiments. The inspection apparatus 10 may include a fixture 18 for supporting the component 12 during data acquisition, the fixture 18 including known markings 20 defining a coordinate system for orienting the acquired data in space. The 2D nondestructive inspection element 14 is used to produce a plurality of two-dimensional images of the component 12 from a number of different views adequate to cover all surfaces of the component 12 to be inspected. In one embodiment the two-dimensional images are digital color photographs. In another embodiment the two-dimensional images are three or more black-and-white images illuminated on the same surface using three or more known colors in such a way that the multiple colors can be processed to produce digital color photographs. The 3D dimensional measurement element 16 is used to produce a three-dimensional model (data cloud) representing the actual surfaces of component 12. A processing element 22 may be used to apply the two-dimensional images onto the three-dimensional model to create a virtual component that may be stored in a database 23 and viewed and manipulated on a display 24. In some embodiments the 2D and 3D mapping information is obtained directly during data acquisition, such as when texture (color) data is acquired synchronously with 3D geometric data on a pixel-by-pixel basis; i.e. for each 3D surface point a corresponding red-green-blue color value may be acquired. The processing element 22 may be used for 3D image computation and for applying the various 2D images onto the computed 3D surface in a manner that provides a smooth transition between adjoining 2D images (also referred to as stitching). The virtual component may be manipulated in a manner similar to any prior art 3D solid model or wire frame. An inspector may use a data analysis element 26 to accomplish an inspection of the virtual component, including the exchange of data with a statistical analysis element 28, which may include archive, operational history, and/or engineering and design information. One may appreciate that the various elements of apparatus 10 may be all located together or some elements may be remote from other elements, such as by linking various elements together via a data communication system such as the Internet.

Prior art 3D dimensional measurement systems lack the ability to characterize any condition of the surface of a component, other than simply determining where the surface exists in space. While such prior art systems are useful for quantifying geometry, they lack the ability to support typical visual inspection requirements. Visual inspections depend upon the ability of the inspector to evaluate visual clues related to the amplitude and color of light reflected from the surface of a component, in order to enable the inspector to make an overall condition assessment, to determine the severity and extent of degradation, and to detect and to characterize visible defects. Assessment of such visual clues, together with the use of observed and measured surface dimensional information, is essential to achieving an accurate and complete evaluation of a component. The inspection apparatus 10 of FIG. 1 allows the inspector to perform an inspection of the real component by accessing and manipulating the virtual component, since all information necessary to perform such an inspection is available via the inspection apparatus 10. Furthermore, accurate records of the inspection can be archived and compared to previous and future inspection results, such as when comparing an as-manufactured condition, an as-repaired condition, and various as-found conditions associated with varying service exposures. Whereas prior art visual inspections are subjective and the data is fugitive, an apparatus 10 of the present invention provides to visual inspections an empirical time-and-condition dimension that has been lacking from prior art systems and methods.

The integration of a three dimensional model of a component with nondestructive inspection information has not been attempted previously, to the knowledge of the present inventors. For the embodiment of integrating 2D digital photographs onto a 3D dimensional model, it is expected that a plurality of 2D pictures from a plurality of views from one or more cameras will be necessary. Spatial resolution of approximately 0.5 mm may be used for general area defects, such as foreign object damage (FOD), missing material, holes, loss or spallation of coatings, burns, oxidation, erosion, corrosion, foreign material buildup, dents, gouges, scratches and pitting, for example. Spatial resolution of approximately 0.01 mm may be preferred for localized and linear indications, such as low cycle fatigue cracks, thermal-mechanical fatigue cracks, high cycle fatigue cracks, creep rupture cracks, coating craze cracks, thermal barrier coating cracks, and corrosion cracks, for example. Spatial resolution of approximately 0.001 mm may be preferred as a substitute NDE method for tightly closed high-cycle fatigue cracks which sometimes exhibiting narrow surface features, or in areas where the component design limits require the detection of very small defects. Existing or artificial light may be used to illuminate the component surfaces, and optical lenses and filters may be used on the light source and the digital imager to achieve a desired sensitivity or resolution. The invention may use add-on or selectable lenses and filters to provide special color lighting (i.e. specific wavelength or wavelength combinations and bandwidths), spatial structured lighting (e.g. stripes, angles, shadowing, highlighting, polarizations) to aid in the imaging of surface conditions, degradations or defects as needed, based upon the absorption and reflectivity of these conditions and the geometry and surface texture of the component.

The invention may utilize 2D inspection images from a sufficient number of angles relative to the actual component to provide full coverage of the 3D component surface(s) being inspected, which may be the entire surface of the component or only selected surface(s) of interest. For a gas turbine blade, for example, it is expected that 16 to 18 images may be necessary to obtain adequate photographic images of all of the surfaces of the blade. In one embodiment, it may be possible to align the edges of adjacent photographs precisely so that the 2D photography data is seamlessly available for the entire 3D surface area. This may not be a practical approach for most applications, so in most embodiments some overlap of adjacent 2D inspection data may be digitally stitched to provide a continuous 2D image in the region of overlap. Special software may be used to combine the acquired 2D images into a seamless map of image data points (pixels) sufficient to cover the 3D component surfaces. Various averaging or smoothing processes may be used to accomplish such stitching, with appropriate hue, saturation and/or luminance adjustments being made to the adjoined data as appropriate. The combined maps will be associated with the geometrically corrected surface points rendered as a solid model from the 3D dimensional measurements, so that the resulting data file is harmonized to 3D dimensions and 2D surface mapping, and the graphical presentation provides a virtual 3D solid model of the actual appearance of the tested component at the time of the test. For components having non-critical regions or regions where no inspection is required, it may be possible to orient the edges of the 2D photography data within such non-critical or non-inspected regions, thereby simplifying or rendering moot the issue of 2D data stitching.

The invention may also include component identification number, time, date and test system operator identification as part of the data file and display. The component identification number may be provided as an input or by image recognition software capable of reading a component identification marking, such as a cast or machined or marked alphanumeric or barcode.

The invention may store, display, manipulate, measure, analyze and annotate the combined 3D dimensions and 2D surface images for individual component assessment, comparative assessment based on manufacturing and handling conditions, comparative assessment based on environmental or service conditions, statistical comparisons based upon a variety of conditions among similar component populations, such as location of degradations or defects on the surface of the component and statistical comparisons based on similar components throughout a population of components. The invention may provide the ability to display comparative virtual image results of two or more tests as overlays or differential displays for comparative analysis. The invention may allow the operator to mark the virtual 3D solid model based upon an evaluation and analysis of the image, for identification of the location, size, shape, orientation and/or extent of degradations and defects or other conditions of interest. The invention may store these results for future display on an image of the virtual component and for statistical comparison with multiple locations on the tested component and/or with other similar components tested. The invention may provide the ability to display statistical results from one or more components, with analysis results of degradations and defects being displayed in their virtual locations of the mapped surface of the 3D solid model.

The invention may provide printouts, common image files (e.g. TIFF, GIF, bitmaps) for use in reports or other digital computer applications and (e.g. IGES or STL files) for engineering design interface. The invention may provide for graphical, keyboard, mouse and other known human interfaces to display, manipulate and enhance the virtual component on computer displays, and may provide tools for identifying, labeling, measuring and storing degradations, defects and/or other conditions of interest as individual items and for recalling these items for display at a later time or for use in comparative statistical analyses.

The invention may be used to image industrial components such as, but not limited to, gas turbine engine components, such as blades and vanes used in the turbine and compressor sections of the machine and combustion section components including nozzles, baskets, transitions and combustion chamber liner components. Components may be imaged in any of the conditions that are found throughout their lives, including: as-cast; as-machined; as-assembled; before and after coating applications; before and after exposure to environmental and service conditions; before, during and after repair operations; and in conditions where degradation or defects have rendered the component unable to continue to perform its intended function, or where the conditions have changed due to repair or service operations in which it is unknown whether the component is in a condition able or unable to continue to perform its intended function.

Figure 2:
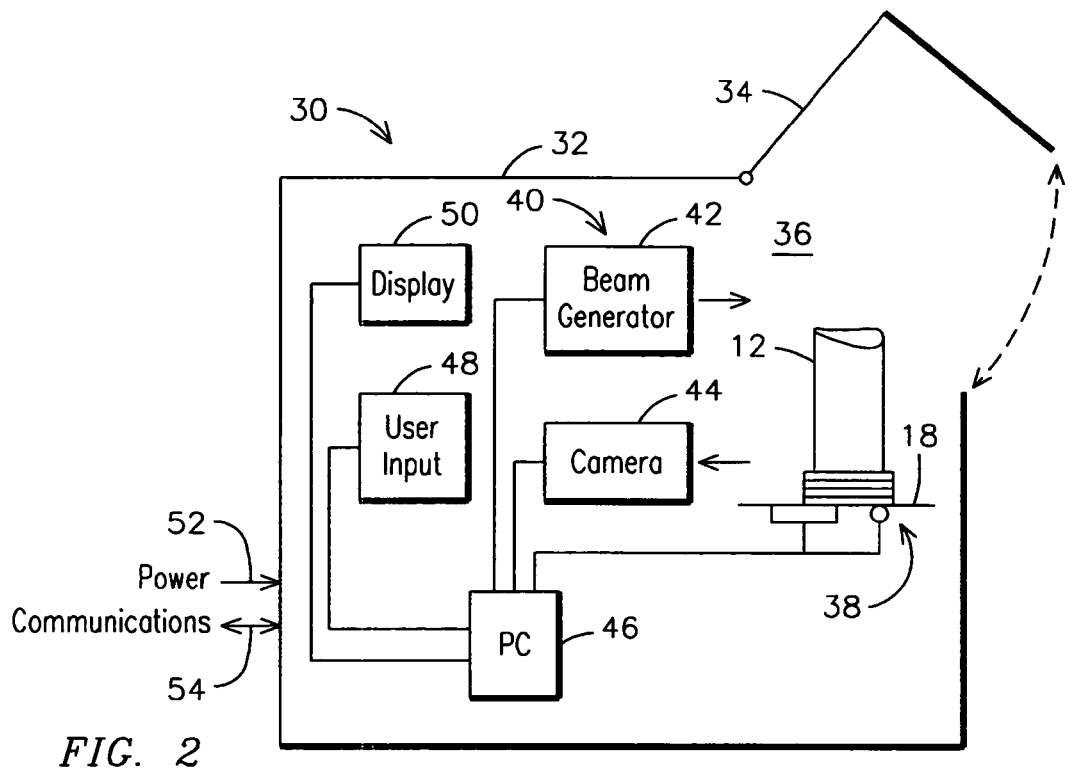
FIG. 2 is a schematic illustration of an inspection apparatus.

FIG. 2 is a schematic illustration of an inspection apparatus 30 of the present invention that may be used for the inspection of components such as a gas turbine blade or vane 12. The inspection apparatus 30 is integrated into a frame or cabinet 32 having a hinged or otherwise moveable access cover 34 that facilitates the placement and removal of test objects when in an open position and that blocks ambient light from the test chamber 36 when in a closed position. The test object is mounted onto a fixture 18 for testing. The fixture includes a multi-axis positioning apparatus 38 for moving the test object into a plurality of positions relative to a data acquisition element 40. The data acquisition element 40 provides the capability for generating the 2D and the 3D data discussed above, and may include a beam generator 42 and a camera 44 in one embodiment. The inspection apparatus 30 also includes a processor assembled into the cabinet 32, such as a known industrial PC 46, and associated input and output devices 48, 50 such as a keyboard and liquid crystal display screen, for example. Power and external communication connections 52, 54 are also provided, allowing the inspection apparatus 30 to be used as part of a larger component analysis system and to provide for communications with information technology networks. Other embodiments may include other light sources within the cabinet 32, such as a UVA lamp for example. Software enabling the various functions of the invention as described herein may be loaded onto a memory device of the industrial PC 46.

Figure 3:
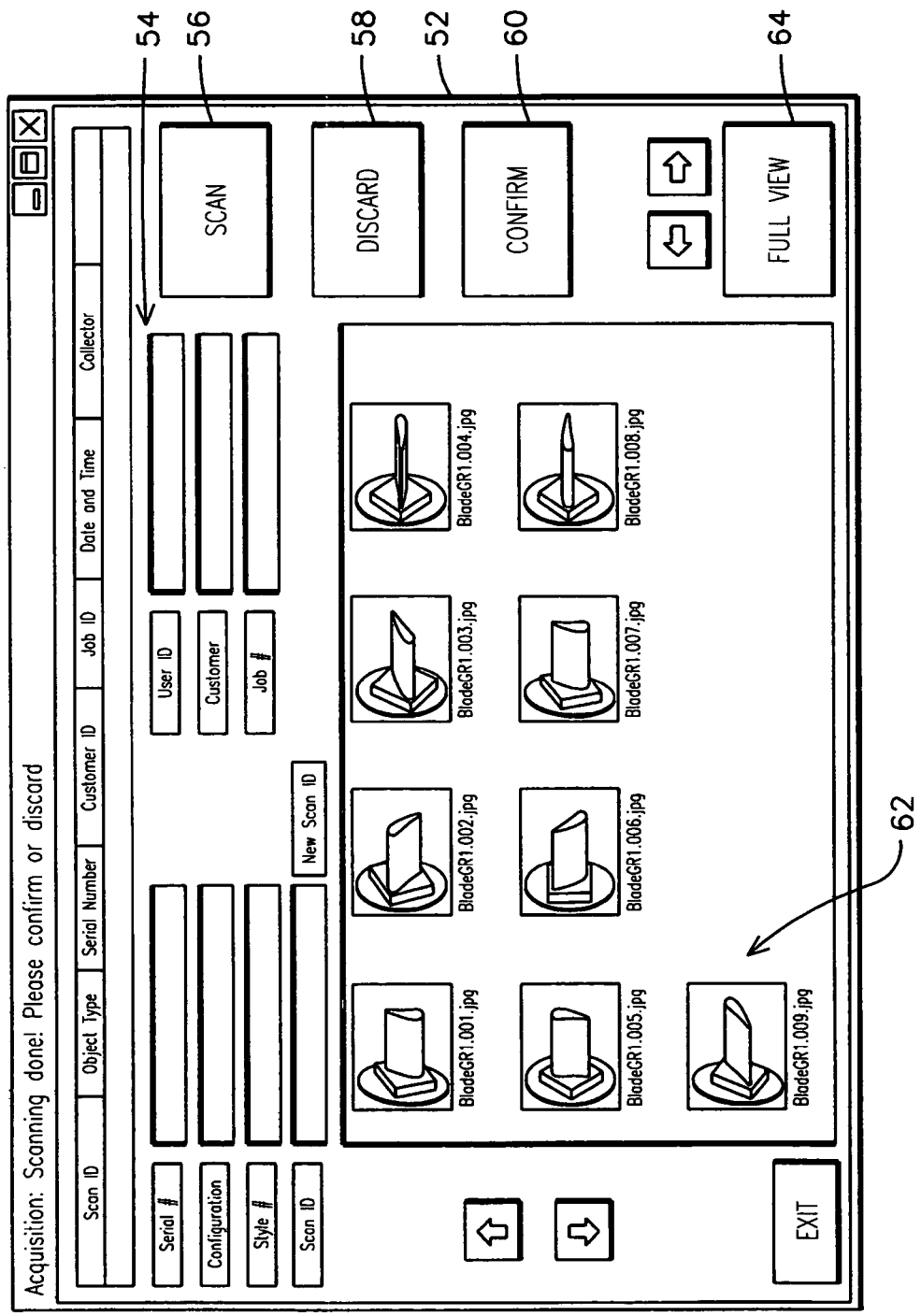
FIG. 3 is a screen display from the inspection apparatus of FIG. 2 being used in a data acquisition mode.

FIG. 3 illustrates a display screen image 52 that may be shown on display 24 as part of the nondestructive inspection element 14 of one embodiment of the inspection apparatus 10 of FIG. 1, or on the display 50 of FIG. 2, when it is being used in a 2D data acquisition mode. Header information 54 may include identification of the test object, customer, operator, etc. Operation controls may include touch screen buttons for initiating a data scan 56, for discarding data 58 and for confirming/saving data 60. Thumbnail displays 62 may be used to show all of the data (pictures) obtained from various scan angles necessary to provide complete coverage of the desired inspection surfaces. Alternatively, a larger display of a single view may be shown in the same region by selecting from among the thumbnail displays 62 and activating the full view button 64.

Figure 4:
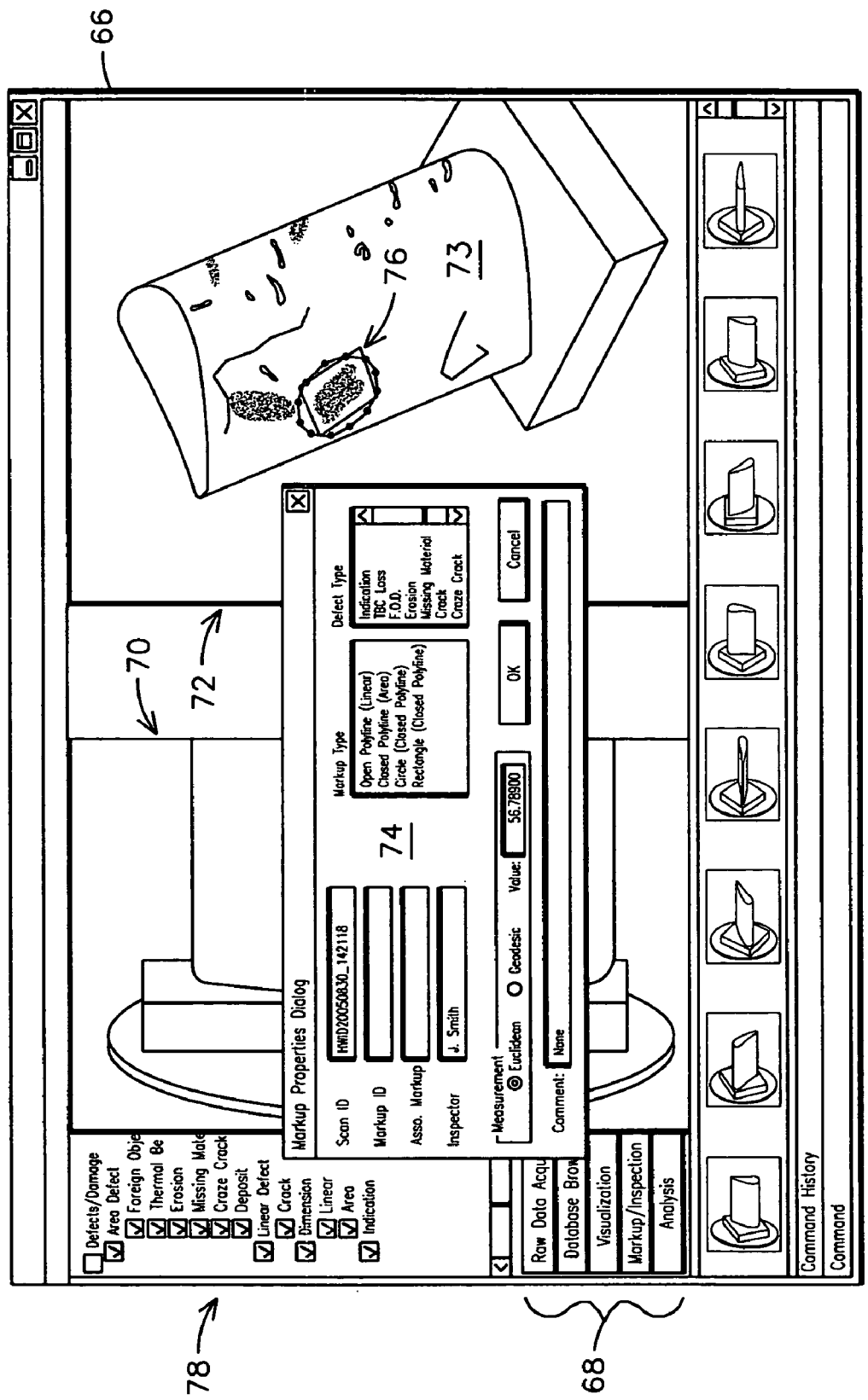
FIG. 4 is a screen display from the inspection apparatus of FIG. 2 being used in a markup/inspection mode.

FIG. 4 illustrates a display screen image 66 that may be shown on display 24 as part of the data analysis element 26 of one embodiment of the inspection apparatus 10 of FIG. 1, or on the display 50 of FIG. 2, when it is being used in an inspection/markup mode. Another embodiment of the inspections allows the inspection/markup mode to be done on a separate PC or engineering workstation based analysis system by transferring 2D-3D files using common portable file storage devices, local area networks (LAN) or wide area networks (WAN), or other digital data transfer methods. The mode of operation is selected from among other choices via a plurality of mode selection buttons 68. In the inspection/markup mode, both 2D and 3D views 70, 72 of the virtual component 73 may be displayed simultaneously, with the operator having the capability of rotating the 3D view to any desired point of view. Once a region of the component surface is identified as having a distinguishable feature of interest in either a 2D or 3D view, that region of the component surface may be marked directly onto the screen image, such as by the use of a Markup Properties Dialog window 74. Predefined markup region shapes and/or sizes may be selectable via menu, and/or the operator may have the flexibility to draw the markup region 76 by freehand drawing directly onto the 2D or 3D image, such as via a mouse command. The marked up region is then associated with a type of defect/damage, such as by selecting from a predefined menu 78 or by the operator inputting a desired command. A markup region 76 defined in any view is automatically configured into the 3D virtual component model and is thus displayable in any other 2D or 3D view.

By common digital data organization methods, various markup regions may be separately organized into layers for presentation and statistical analysis of a single component or a group of components. For example, one embodiment of the invention may allow for the display of a density map of all similar defects found in a fleet of similar components in a single display of a representative component, thus allowing an observer to easily identify regions of such components that are susceptible to such defects. Alternatively, defects of only a certain type may be displayed selectively. Statistics may be generated automatically, such as percentage of the surface area containing a certain type of defect. Defects may be categorized as to severity, such as length of cracks, depth of erosion, size of pits, etc. and appropriate statistics generated for analysis. The progress of defects over time may be presented when multiple inspections are performed on a single component. Regions of the component may be identified prior to the inspection, such as to define inspection zones for an inspector. Such inspection zones may guide the inspector to varying inspection procedures/criteria for each zone, such as by allowing the inspector to "right click" a mouse indicator positioned over such zone to display a viewing window including such inspection procedures/criteria.

While prior art visual inspections are fugitive, the present invention allows the virtual component to be stored through time. This facilitates direct and empirical comparisons of time-displaced and location-displaced inspections. Furthermore, multiple inspectors may perform multiple inspections on the same component under the same conditions, even if the inspectors are located in different locations at different times. If inspection criteria change over time, a component may be re-inspected by simply performing a new inspection with the new criteria on the stored virtual component.

The power of modern optical devices may be exploited with the present invention to provide enhanced inspection capabilities that exceed those of an unaided human inspector. For example, very high resolution 2D images may be acquired and analyzed in combination with a zoom capability in order to allow the inspector of the virtual component to clearly view surface features that are too small for accurate observation with the unaided human eye. Prior art visual inspections may incorporate a penetrating dye in order to improve the visibility of very small and/or tight cracks. However, the use of penetrating dye consumes time and money and introduces a contaminant onto the component surface. The use of high resolution imaging and zoom viewing capability in one embodiment of the present invention precludes the need for such dye by allowing the inspector to enlarge an image of a portion of the component surface to a degree that makes such small and/or tight cracks visible without the need for a highlighting dye. In another embodiment, one or more of the hue, saturation and/or luminance may be manipulated during an inspection to optimize the visibility of a surface feature.

Figure 5:
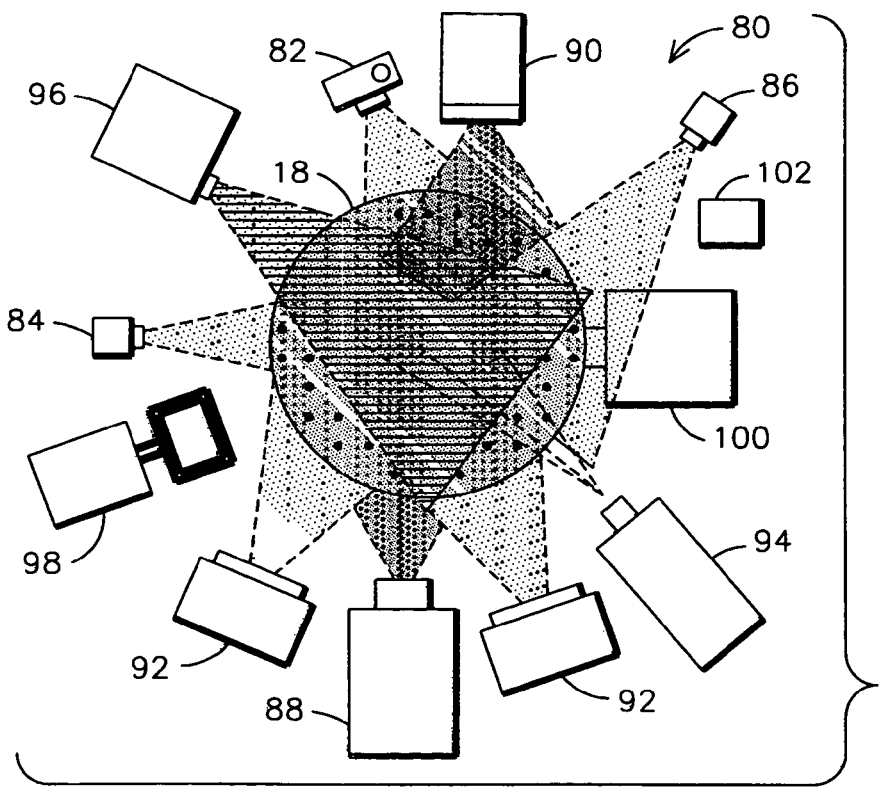
FIG. 5 is a schematic illustration of an inspection apparatus.

FIG. 5 is a schematic illustration of an inspection apparatus 80 wherein a plurality of forms of nondestructive testing data may be acquired for use with a 3D model of a component being inspected. A fixture 18 for holding a component to be inspected is disposed within the fields of view of a variety of data acquisition devices, including but not necessarily being limited to: a high resolution visible light color and/or ultraviolet light camera 82; a high resolution visible light black and white camera 84; a low resolution visible light camera 86 optionally with pan/tilt capability; an infrared light camera 88; a UVA light source 90, one or more flash lamps 92 for area heating for thermography; a laser light source 94 for point source heating for thermography; one or more projector (beamer) 96 for selectively projecting color light, white light, ultraviolet light (e.g. UVA), and/or structured light; an induction thermography energy source 98; a contact thermography energy source 100; etc. Another embodiment of the invention allows for the placement of a probe 102 for obtaining single-point nondestructive testing data, including from eddy current, magnetic, capacitive, hardness, thickness and/or ultrasonic probes to be mapped onto the 2D images and 3D virtual model. Additionally, such single-point data can be used to construct virtual image maps visually tracking the position of the probes using the visual processing elements of the present invention or by the addition of known electromechanical, hydraulic or pneumatic manipulators and position encoding devices. The various forms of 2D nondestructive data/images produced by these devices may be associated with a 3D model of the tested component, such as is accomplished in the image processing element 22 of FIG. 1. Embodiments of the invention may thus have the capability of mapping a plurality of 2D inspection images, such as in the form of multiple digital layers, onto a 3D surface of a solid model of the component, for presentation to an inspector either sequentially or simultaneously or in various selective combinations. One may appreciate that various forms of surface features may appear differently under various forms of nondestructive imaging, and that an inspector advantageously may be able to utilize such differences to diagnose a condition of a component. For example, a surface feature that appears in a thermography image but not in a visible light photograph may be interpreted as a subsurface feature. An inspector may further exploit the capabilities of such an inspection apparatus 80 by performing a first inspection of a surface area of a virtual component displayed with a surface as produced using a first type of 2D inspection data, such as relatively lower resolution color photographic data; followed by a second inspection of only selected regions of the surface area that are found to display features of interest during the first inspection, with the second inspection being performed using a second view of the virtual component displayed with a surface as produced using a second type of 2D inspection data, such as relatively higher resolution black and white or color photographic data. Any combination of displays of the virtual component may be used in any order as may be found to function effectively to diagnose conditions of interest. Regions found to contain features of interest in any view may be marked as described above, with such information being saved digitally in a manner that facilitates the sorting, grouping and analyzing of such data for one or more such components.

Analysis of the inspection data may include the evaluation of the data in combination with related component data. The terms "component data" and "component information" are used herein to include design, operating history, maintenance and repair data and information. Such related component data may be stored in a database 23 for use by the data analysis element 26. In an embodiment used for inspecting gas turbine blades, the design basis operating temperature at the surface of the blade may be selectively displayed as a further digital layer on the 3D model surface; thereby facilitating an evaluation of 2D inspection data with consideration of the operating temperature experienced at the point of a feature of interest on the surface of the blade.

The present invention allows for the use of both relatively high resolution inspection data and relatively low resolution inspection data. For example, lower resolution data may be acquired and analyzed in regions of a component that are of relatively lower concern, such as regions of low stress or regions that historically are not subject to degradation or that are subject to types of degradation that are only of concern when they reach larger sizes, such as general area erosion for example. Selected regions of a component may be subjected to a higher resolution inspection, such as critical or highly stressed areas. In the embodiment of an inspection of a gas turbine blade, for example, the surface areas of the airfoil may be inspected at a first level of optical resolution, whereas the filet weld area between the airfoil and the platform of the blade may be inspected at a second higher level of optical resolution.

In one embodiment of the invention, a high resolution black and white camera 84 is used to take three sequential photographs from each view angle; one each photograph being taken with the component being illuminated by a projector 96 with red, green and blue light respectively. The three images are then digitally combined to create a color image of the component in lieu of creating such an image with a high resolution color camera 82.

In addition to, or in lieu of, the mapping of 2D inspection data onto the surface of the virtual component, three dimensional nondestructive inspection data may be merged with the 3D solid model of the component. The 3D inspection data may include data from radiography, computed tomography, ultrasonic inspection or other forms of volumetric nondestructive examination. Such information may prove useful to an inspector for analyzing surface feature indications, since subsurface structures may influence surface examination results. For example, a linear indication visible on the surface of the virtual component when thermography inspection data is mapped onto the 3D solid model of the component may be understood to be the result of a subsurface reinforcing structure when the virtual component is also viewed in a sectional view using the results of an X-ray examination of the component. In this example, the 3D solid model is merged with both 2D surface inspection information and with 3D internal inspection information.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. An inspection method comprising:
   acquiring a three dimensional model of a surface of a component;
   acquiring inspection data from the component;
   associating the inspection data with the three dimensional model to create a display of a virtual component having a surface shape corresponding to the surface of the component and having a surface appearance corresponding to the inspection data;
   performing an evaluation of the virtual component;
   evaluating the virtual component to identify areas of distinguishable surface features on the surface of the virtual component;
   separately associating each of the areas of distinguishable surface features with the three dimensional model surface; and
   selectively illustrating one or more of the areas of distinguishable surface features on the surface of the virtual component on the display.

2. The method of claim 1, further comprising:
   associating a result of the evaluation with the three dimensional model; and
   illustrating the result of the evaluation as an image on the surface of the virtual component.

3. The method of claim 1, further comprising:
   acquiring two dimensional digital photographic information from a plurality of different views of the component;
   associating the photographic information with the three dimensional model of the component to create the virtual component; and
   performing a visual inspection of the virtual component by manipulating the display.

4. The method of claim 3, further comprising providing a zoom function in the display to enhance the inspection.

5. The method of claim 3, further comprising manipulating at least one of hue, saturation and luminance of the displayed photographic information to enhance the inspection.

6. The method of claim 3, further comprising:
   acquiring two dimensional visible light digital photographic information and two dimensional ultraviolet light photographic information for inspection of a component processed with a fluorescent dye;
   associating both the two dimensional visible light and ultraviolet light digital photographic information with the three dimensional model of the component to create the virtual component for performing the visual inspection.

7. The method of claim 1, further comprising:
   acquiring at least two different types of two dimensional inspection data from the component; and
   associating the at least two different types of two dimensional inspection data with the three dimensional model to create a display of a virtual component having a surface appearance corresponding to a selected one or more of the at least two different types of two dimensional inspection data.

8. The method of claim 1, further comprising associating a two dimensional display of component data with the three dimensional model to create the virtual component.

9. The method of claim 1, further comprising performing the evaluation of the virtual component after the surface of the component has changed from a condition in existence at the time of the step of acquiring the inspection data from the component.

10. An inspection apparatus comprising:
    a dimensional measurement element adapted to produce a three dimensional model of a surface of a component;
    a nondestructive inspection element adapted to produce a number of two dimensional nondestructive test images responsive to a condition of the component;
    a processor for associating the two dimensional nondestructive test images with a surface of the three dimensional model for display as a virtual component,
    wherein the nondestructive inspection element comprises a visible light camera and the nondestructive test images comprise a digital photograph,
    wherein the nondestructive inspection element comprises a black and white camera and a projector for selectively illuminating the surface of the component with red, green and blue light.

11. The apparatus of claim 10, further comprising a fixture for supporting the component, the fixture comprising known markings defining a coordinate system for orienting data acquired from the component.

12. The apparatus of claim 10, further comprising a data analysis element for manipulating the display of the virtual component for performing an inspection.

13. The apparatus of claim 12, further comprising a statistical analysis element in communication with the data analysis element.

14. The apparatus of claim 12, wherein the dimensional measurement element comprises a structured light projector and camera.

15. An inspection apparatus comprising:
a dimensional measurement element adapted to produce a three dimensional model of a surface of a component;
a nondestructive inspection element adapted to produce a number of two dimensional nondestructive test images responsive to a condition of the component;
a processor for associating the two dimensional nondestructive test images with a surface of the three dimensional model for display as a virtual component, wherein the nondestructive inspection element comprises at least one of the group consisting of a color visible light camera, a black and white visible light camera, an infrared light camera, and an ultraviolet light camera.

16. An inspection apparatus comprising:
a means for acquiring a three dimensional model of a component;
a means for acquiring two dimensional data associated with a surface of the component;
a means for creating a display of a virtual component having a surface shape corresponding to the three dimensional model and having a surface appearance corresponding to the two dimensional data;
a means for manipulating the display for performing an evaluation of the virtual component;
a means for associating a result of the evaluation with the three dimensional model for display on the surface of the virtual component;
the means for acquiring two dimensional data comprises a means for acquiring inspection data from the component and a means for acquiring component data associated with the component; and
the means for creating a display comprising a means for selectively displaying the inspection data and the component data on the surface of the virtual component.

* * * * *